(12) United States Patent
Poole et al.

(10) Patent No.: US 9,964,494 B1
(45) Date of Patent: May 8, 2018

(54) THERMALLY EMISSIVE SENSING MATERIALS FOR CHEMICAL SPECTROSCOPY ANALYSIS

(71) Applicant: The United States of America Department of Energy, Washington, DC (US)

(72) Inventors: Zsolt Poole, Pittsburgh, PA (US); Paul R. Ohodnicki, Allison Park, PA (US)

(73) Assignee: U.S. Department of Energy, Washington, DC (US)

( * ) Notice: Subject to any disclaimer, the term of this patent is extended or adjusted under 35 U.S.C. 154(b) by 49 days.

(21) Appl. No.: 15/160,389

(22) Filed: May 20, 2016

Related U.S. Application Data

(60) Provisional application No. 62/233,484, filed on Sep. 28, 2015.

(51) Int. Cl.
G01N 21/00 (2006.01)
G01N 21/71 (2006.01)

(52) U.S. Cl.
CPC .................. G01N 21/71 (2013.01)

(58) Field of Classification Search
CPC .. G01M 15/102; G01M 15/108; G01M 15/04; G01N 21/716; G01N 21/71; G01N 33/0004; G01N 33/0036
See application file for complete search history.

(56) References Cited

U.S. PATENT DOCUMENTS

| | | | | |
|---|---|---|---|---|
| 2011/0292965 | A1* | 12/2011 | Mihailov | G01D 3/0365 374/121 |
| 2013/0092846 | A1* | 4/2013 | Henning | G01N 21/6408 250/458.1 |
| 2014/0246572 | A1* | 9/2014 | Yamamoto | G01B 11/16 250/227.14 |

OTHER PUBLICATIONS

Ohodnicki, Paul R. et al. "In-situ and ex-situ characterization of TiO2 and Au nanoparticle incorporated TiO2 thin films for optical gas sensing at extreme temperatures." Journal of Applied Physics (2012) 111 064320. (Year: 2012).*

Shimizu, Yasuhiro et al. "Oxygen sensor using perovskite-type oxides." Chapter 5 in Fundamentals and Applications of Chemical Sensors ACS Symposium Series. ACS 1986, pp. 83-100. (Year: 1986).*

Yan, Qiangu et al. "Optical fiber evanescent wave absorption spectrometry of nanocrystalline tin oxide thin films for selective hydrogen sensing in high temperature gas samples." Talanta (2009) 77 953-961. (Year: 2009).*

* cited by examiner

*Primary Examiner* — Christopher Adam Hixson
(74) *Attorney, Agent, or Firm* — Jacob A. Heafner; Michael J. Dobbs; Brian J. Lally

(57) ABSTRACT

A sensor using thermally emissive materials for chemical spectroscopy analysis includes an emissive material, wherein the emissive material includes the thermally emissive materials which emit electromagnetic radiation, wherein the electromagnetic radiation is modified due to chemical composition in an environment; and a detector adapted to detect the electromagnetic radiation, wherein the electromagnetic radiation is indicative of the chemical interaction changes and hence chemical composition and/or chemical composition changes of the environment. The emissive material can be utilized with an optical fiber sensor, with the optical fiber sensor operating without the emissive material probed with a light source external to the material.

16 Claims, 12 Drawing Sheets

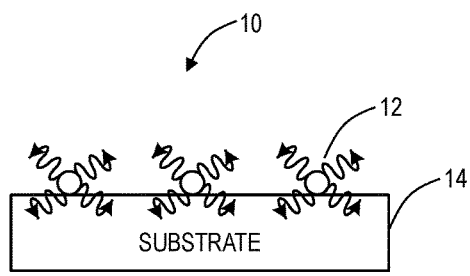
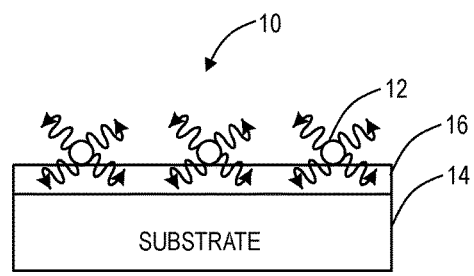
FIG. 1A  FIG. 1B
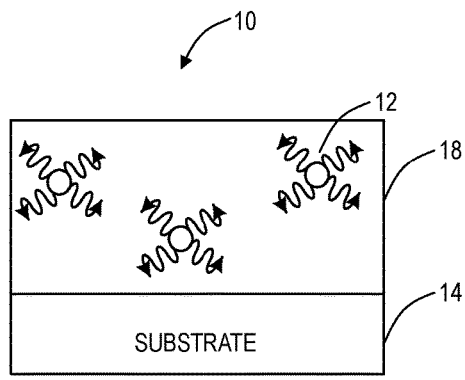
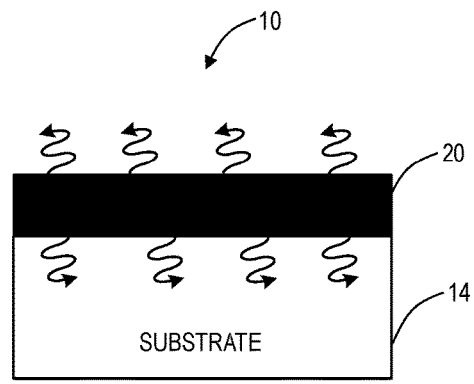
FIG. 1C  FIG. 1D
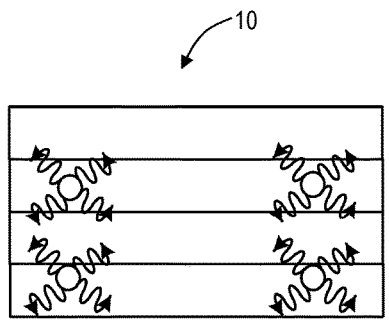
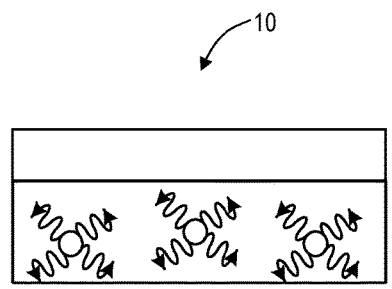
FIG. 1E  FIG. 1F

THERMALLY EMISSIVE SENSING MATERIALS FOR CHEMICAL SPECTROSCOPY ANALYSIS

CROSS-REFERENCE TO RELATED APPLICATION(S)

The present patent/application claims priority to U.S. Provisional Patent No. 62/233,484 filed Sep. 28, 2015, and entitled "A METHOD FOR PERFORMING BLACKBODY THERMAL EMISSION BASED CHEMICAL SPECTROSCOPY ANALYSIS AND OPTICAL FIBER BASED SENSORS FOR CARRYING OUT THE SAME," the contents of which are incorporated by reference.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE DISCLOSURE

The present disclosure generally relates to chemical spectroscopy systems and methods. More particularly, the present disclosure relates to thermally emissive materials for chemical spectroscopy analysis which emit electromagnetic radiation indicative of chemical interaction changes of a surrounding environment, without requiring external illumination to probe the material. That is, the thermally emissive materials generate light from the thermal energy of the surrounding, and the light emitted by the thermally emissive materials is indicative of the chemical composition of the environment. In an exemplary embodiment, the thermally emissive sensing materials are integrated with an optical fiber platform in an evanescent sensor configuration. It is contemplated that there are numerous methods of implementation by which the environmentally characteristic thermal emission of a chosen material can be observed.

BACKGROUND OF THE DISCLOSURE

There is an existing need for sensors and monitoring schemes for high temperature and harsh environments to address a broad range of applications such as, for example, fossil-based power generation, industrial manufacturing, aerospace/aviation, and the like. Some specific applications for such sensors and spectroscopic techniques include advanced combustion, solid oxide fuel cells, gas turbines, boiler systems, chemical looping, etc. A common need in all cases is the ability to monitor critical process parameters under in-situ conditions which may involve temperatures ranging from, but not limited to, 500-1500° C. (as well as different temperature ranges) depending upon the application of interest. Hydrogen-based energy generation systems such as solid oxide fuel cells are attractive alternatives to conventional thermal based power generation such as through coal combustion, for example, due to their relatively low environmental impact and the potential for higher efficiencies. However, there is a definite lack of sensors that can provide fast in-situ systemic hydrogen utilization feedback at high temperatures such as above 500° C. Although, in general, any temperature can be viable for emissivity monitoring, and is only limited by the availability of detectors and the thermal emission profile of the material in question, which would dictate the choice of the material constituents. Therefore, the proposed method can be ubiquitous across a large span of temperatures.

Optical-based sensing methodologies have emerged as a superior technology for harsh environment sensing due to a number of associated advantages relative to more traditional electrochemical and electrical-based sensing approaches. Such advantages include the lack of electrical wiring or components at the sensing location, mitigated risk of electrical sparking in flammable gas environments, and the ability to perform broad/multiple wavelength and/or distributed interrogation of sensor devices and materials, as material interactions with light provide a much richer parameter space. Although optical-based sensing methodologies have a number of inherent advantages, a key weakness is often the need for an optical light source which can be costly and in some cases can present inherent instabilities over time that must be addressed. While relatively low-cost solutions do exist such as inexpensive halogen sources and photodiodes, it would be advantageous to eliminate the need for a light source to greatly simplify the optical sensor design and to reduce overall costs.

Thermal emission enhancement and thermal spectra tailoring have been observed in a variety of materials some of which are micro/nanostructured, heavily doped semiconductors, rare earth doped, quantum dots embedded, and in tandem with nano-gaps to extract the extraordinary near-field thermal emissions. While these techniques can greatly improve on the overall thermal emission and address desired aspects such as spectral specificity using up-conversion, photonic-bandgaps, and isolated decay channels for application such as in Thermophotovoltaic (TPV) systems, it has not previously been demonstrated that the thermal emission of a material can be significantly altered by changes in the gaseous chemistry of its environment at elevated temperatures. Aside from the basic considerations outlined in the well-known Kirchoff's relationship between emissivity and absorptivity of matter in thermal equilibrium, the current thermodynamic literature does not discuss how the microscopic material constituents are related to variations in thermal emission and how this may be affected by changes in the chemical constituents of complicated environments that exist in many systems such as in energy conversion applications. For example, a Thermophotovoltaic or Thermoelectric system could also see an efficiency enhancement due to placement of the system or some portion of the system in a chemical environment altering the system's chemical, physical, or electrical property, as contemplated for spectroscopic applications.

BRIEF SUMMARY OF THE DISCLOSURE

In an exemplary embodiment, a sensor using thermally emissive materials for chemical spectroscopy analysis includes an emissive material, wherein the emissive material is one which emits electromagnetic radiation, wherein the electromagnetic radiation is modified due to chemical composition in an environment; and a detector adapted to detect the electromagnetic radiation, wherein the electromagnetic radiation is indicative of the chemical interaction changes and hence chemical composition and/or chemical composition changes of the environment. The emissive material can be utilized with an optical fiber sensor, with the optical fiber sensor operating without an external light source. The optical fiber sensor can include an optical fiber coupled to the detector, wherein the emissive material is one of deposited on a core or the end-face of the optical fiber, coated on the optical fiber, and integrated with the optical fiber to derive information about the chemical composition of the environment. The optical fiber sensor can include an optical fiber coupled to the detector, wherein the emissive material is integrated with one of a core, a cladding, and/or a combination of the core and the cladding of the optical fiber to derive information about the chemical composition of the environment. In some embodiments, the detector can include two detectors each at opposite ends of an optical fiber of the optical fiber sensor which monitors an output from the emissive material to derive information about the chemical composition of the environment and spatial dependence of the chemical composition. The optical fiber sensor can include a distributed optical fiber sensor with a plurality of emissive materials each operating at different wavelengths. The optical fiber can include a bundled fiber with a plurality of optical fibers therein with the emissive material to provide distributed sensing. The optical fiber can also include modifications constituting an "in-fiber" device, such as fiber Bragg gratings, notches, holes, and various other modifications as is known in the art and it is contemplated that these modifications can alter the emissive properties of the fiber sensor and can be used in conjunction with other emissive coatings. In some cases, the thermally emissive material itself can be structured to alter the emissive properties, as is known in the art that the emissivity and the spectral profile of the emissivity of materials can be engineered by structuring.

The emissive material interacts with environmental chemistry to provide an altered emissivity. When integrated with the optical fiber sensor platform in an evanescent configuration (e.g. deposited within the evanescent penetration depth of the fiber core), the emissivity can be observed via high isolation with respect to background interferences through tunneling to the optical fiber sensor by overlapping the emissive material near-field and optical fiber evanescent regions. The emissive material can include one of $TiO_2$, $Pd$—$TiO_2$, and $Au$—$TiO_2$ nanocomposites, with varied properties including electronic and ionic conductivity, hydrogen absorptivity, and localized surface plasmon resonance (LSPR) based activity in nitrogen and in oxygen containing high-temperature environments. The emissive material can include a perovskite oxide. The emissive material can include strontium titanate ($SrTiO_3$) or doped $SrTiO_3$. The emissive material can include one of the thermally emissive sensing materials directly deposited on a material, the thermally emissive sensing materials on an underlayer, the thermally emissive sensing materials embedded in a matrix phase, a monolithic film with the thermally emissive sensing materials, and the thermally emissive sensing materials embedded in a multi-layer stack and/or overcoated by another thin film layer. The emissive material can also include modifications to an optical fiber core and/or cladding material composition (e.g. rare earth doping, transition metal doping, metallic nanoparticle doping) or associated defect structure through processing (e.g. thermal treatments in reactive gas compositions, engineered laser treatments, thermal treatments in a mechanical strain).

In another exemplary embodiment, a method for chemical spectroscopy analysis with a sensor using thermally emissive sensing materials includes emitting radiation by the thermally emissive sensing materials responsive to thermal energy which is altered based on chemical interaction changes in an environment; and detecting the radiation by a detector, wherein the electromagnetic radiation is indicative of the chemical interaction changes. The method can further include detecting the radiation by the detector coupled to an optical fiber of an optical fiber sensor, wherein the detector detects light emitted thermally by the sensing material. The emissive material can be one of deposited on a core of the optical fiber, coated on the optical fiber, and integrated with the optical fiber. The emissive material interacts with environment chemistry to provide an altered emissivity observed via high isolation through tunneling to the optical fiber by overlapping the emissive material near-field and optical fiber evanescent regions. The emissive material may also directly emit light into the optical fiber, or the emitted light can be coupled into the optical fiber by other mechanisms such as scattering. The emissive material can include one of $TiO_2$, $Pd$—$TiO_2$, and $Au$—$TiO_2$ nanocomposites, with varied properties including electronic/ionic conductivity, hydrogen absorptivity, and localized surface plasmon resonance (LSPR) based activity in nitrogen and in oxygen containing high-temperature environments. The emissive material can include a perovskite oxide. The emissive material can include strontium titanate ($SrTiO_3$) or doped $SrTiO_3$. The emissive material can also include modifications to an optical fiber core and/or cladding material composition (e.g. rare earth doping, transition metal doping, metallic nanoparticle doping) or associated defect structure through processing (e.g. thermal treatments in reactive gas compositions, engineered laser treatments, thermal treatments in a mechanical strain).

In a further exemplary embodiment, a method using thermally emissive sensing materials for chemical spectroscopy analysis include providing an emissive material, wherein the emissive material includes the thermally emissive sensing materials which emit electromagnetic radiation due to chemical interaction changes with an environment; and providing a detector adapted to detect the electromagnetic radiation, wherein the electromagnetic radiation is indicative of the chemical interaction changes.

BRIEF DESCRIPTION OF THE DRAWINGS

The present disclosure is illustrated and described herein with reference to the various drawings, in which like reference numbers are used to denote like system components/method steps, as appropriate, and in which:

FIGS. 1A-1F are diagrams of thermally emissive sensing layers including particulate thermal emitters on a support (FIG. 1A), particulate thermal emitters on an underlayer (FIG. 1B), particular thermal emitters embedded in a matrix phase (FIG. 1C), a monolithic film of a thermally sensing material on a support (FIG. 1D), incorporated in a multilayer stack (FIG. 1E), and under an overlayer (FIG. 1F).

FIG. 7A is a graph of the interaction of a $TiO_2$ thin film, coated on the core of a multimode optical fiber, and observed at visible wavelengths.

DETAILED DESCRIPTION OF THE DISCLOSURE

Figure 2A:
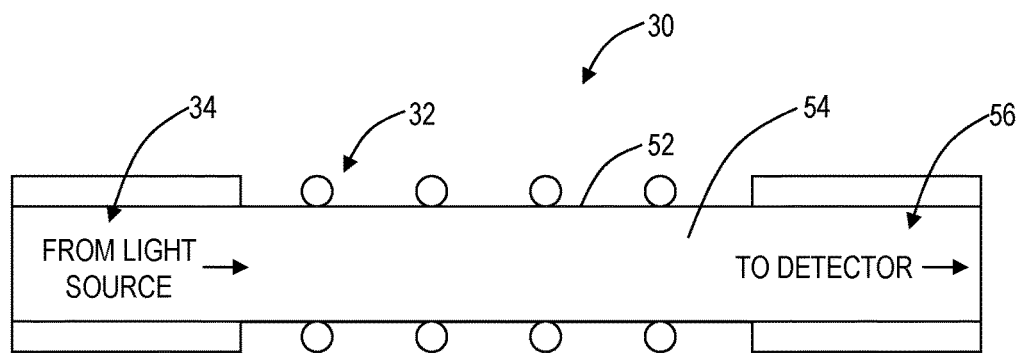
FIGS. 2A-2B are exemplary block diagrams of a conventional evanescent wave absorption spectroscopy based optical fiber sensor employing a light absorbing and/or scattering sensing material and a light source (FIG. 2A) as compared to one exemplary optical fiber sensor exploiting the thermally emissive sensing materials of FIG. 1 thereby eliminating the light source (FIG. 2B).

Again, in various exemplary embodiments, the present disclosure relates to thermally emissive materials which can be used in an optical fiber sensor method and apparatus as well in other applications. The thermally emissive materials exploit the inherent thermally activated light emission of materials and the dependence on effective optical constants of the material through relevant environmental parameters of interest including chemistry, where the effective optical constants can be influenced by changes in the conductivity of the material, density of the material, the chemical identity of the material, a volumetric expansion of the material, and other changes that can take place upon interaction with an environment. In other words, the emissivity of a particular sensor material is monitored directly through optical based methodologies and utilized for optical fiber based sensing without the need for an active optical source (external light probe). Such an approach harvests inherent thermal energy in elevated temperature processes and converts the energy into light emission that can be monitored through standard optical fiber based sensing approaches, for example. Other exemplary embodiments can include emission of a coating on an inside of a furnace or the like which can be monitored. The thermally emissive materials can be incorporated into an engineered film, potentially through nanostructuring, with directivity such that it emits light in the direction needed and also potentially with a desired spectral profile. Such an engineered film can be potentially coated in combustion chambers and in other useful locations.

Exemplary applications of the thermal emission-based chemical spectroscopy analysis include elevated temperature and harsh environment sensing applications such as for determining high temperature gas stream composition in power generation applications (turbines, combustion, solid oxide fuel cells, gasification, etc.), monitoring exhausts of combustion processes such as turbines, industrial manufacturing, etc., using high intensity thermal emitters in relatively lower temperature applications, and the like. The thermal emission-based chemical spectroscopy analysis has application in the visible, near-Infrared (IR), and IR wavelength ranges amongst others.

In an exemplary embodiment, optical sensor devices use thermally emissive sensing materials without requiring external light sources to probe the sensory material. The optical sensor devices provide lower cost, lower power, and less complex optical sensor devices such as for high-temperature applications. The optical sensor devices can also monitor temperature through multi-wavelength and/or broadband interrogation by using the wavelength distribution of thermally emitted light where the emissive material and/or emissive material-optical fiber device. This is because for some wavelengths, the thermal emission will be less or insignificantly affected by changes in the environmental composition than others, as one example. In addition, it may be possible to have an emissive material whose thermal emission is affected by the composition of the environment to still provide a measure of temperature, as well, by examining the shape of the distribution and the location of the thermal emission peak. Temperature characterization can also be used to remove temperature sensitive cross-interferences when interpreting changes associated with the chemical composition of the surrounding environment. The described method can be implemented at any absolute temperature, and the measurement of the emitted light would only be limited by the sensitivity of a detector at the wavelength of interest and the strength of the emission by the emissive material and/or emissive material-optical fiber device. For applications where the thermal emission is weaker, such as lower temperatures, and requiring careful detection, engineering emissivity, and directivity can be used to improve the ease of detection. The optical sensor devices are compatible with remote, and distributed sensing methodologies and can have the well-known advantages of optical-based sensors. Techniques such as principle component analysis can be applied to the measured broadband thermally emitted light in order to reduce or eliminate cross-correlation of the measured response to other parameters (temperature, pressure, other chemical species) that may be changing. The optical sensor devices can provide distributed interrogation capability, for example by monitoring the light emission through both sides of an optical fiber combined with analytical modeling to identify local regions where environmental changes have taken place. Alternatively, distributed interrogation capability can also be provided by (a) a multitude of emissive sensing materials with a spectral emissivity that is distinct at various positions along the fiber and/or (b) integration of emissive sensing materials with devices such as fiber Bragg gratings. In some cases, thermally emissive sensing materials may be spatially localized or even varied at a length-scale that is characteristic of the monitored electromagnetic radiation thereby allowing for spatial localization of chemical spectroscopy information and also spectral tunability of emission profiles.

In various exemplary embodiments, a method and apparatus can include thermally emissive sensing materials deposited on planar substrates. The thermally emissive sensing materials can be coated on a surface of interest to be monitored and measured through imaging spectroscopy. The thermally emissive sensing materials can be integrated with the fiber optic sensing platform to collect emitted light, enabling operation without needing to probe the sensor material with an external light source. The method and apparatus can use the changing sensing material emissivity for chemical composition monitoring of a gas stream, for chemical composition of fluid, and the like.

For thermal emissivity based sensing and spectroscopy, the exploitation of directionally emissive materials such as aligned carbon nanotubes or patterned structures, gratings for example, can provide enhancement in the emitted light and can also be used for thermal emission based sensing based on the modification of some electrical, physical, and or chemical parameter of the emissive materials. In addition, backfilled and or infiltrated directionally emissive materials such as aligned and/or patterned structures can also be used for thermal emission based sensing/chemical spectroscopy. In some cases, such aligned, patterned, and/or spatially varying emissive material structures may be introduced within the cladding or core of an optical fiber.

Thermal Emissivity

Referring to FIGS. 1A-1F, in various exemplary embodiments, diagrams illustrate thermally emissive sensing materials 10 including particulate thermal emitters 12 on a substrate 14 (FIG. 1A), particulate thermal emitters 12 on an underlayer 16 (FIG. 1B), particular thermal emitters 12 embedded in a matrix phase 18 (FIG. 1C), a monolithic film 20 of a thermally sensing material on a substrate 14 (FIG. 1D), the various embodiments incorporated in a multilayer stack (FIG. 1E), and under an overlayer (FIG. 1F). Those of ordinary skill in the art will recognize the various exemplary embodiments presented in FIGS. 1A-1F are for illustration purposes. Various other embodiments are also contemplated, including various combinations of the exemplary embodiments of FIGS. 1A-1F. FIG. 1E can have monolithic layers and particulate layers, in various combinations. There can also be different thickness layers, etc. as desired. The coating may be a structured material, such as by having a porosity. Or by periodic and random structuring to provide an angular dependence to the emissivity, encompassing structuring in 1D, 2D, and 3D geometries. The particulate thermal emitters 12 could be plasmonic nanoparticles, quantum dots, quantum wells, rare-Earth containing nanoparticles and materials, trapped atoms or molecules inside a matrix to constitute a clathrate, rare earth element or transition metal dopants within a matrix, or local defects within a structure, etc. The particular thermal emitters 12 are included in a matrix or material to act as emitters whereas the monolithic film 20 has the entire material acting as an emitter. The monolithic film can be materials possessing a free electron concentration, a material with the property of ionic conductivity, polar materials, materials with surface phonon polaritons, materials with surface plasmon polaritons, and materials containing molecular vibrations amongst others. The particulate thermal emitters 12 are included in another material to act as an emitter, although a relationship between particulate thermal emitters and host may exist that enhances the thermal emissivity and or environmental changes in thermal emissivity. Any material is contemplated herein that has emissive properties based on interaction with an environment with the emissive properties based on chemical interaction changes therein.

The thermally emissive sensing materials 10 generates electromagnetic radiation based on thermal energy and the electromagnetic radiation is emitted to the surrounding environment. The process of converting thermal energy to propagating electromagnetic radiation is accomplished by vibrations and/or oscillations taking place inside said emissive materials. Where, in the case of evanescent thermal radiation it is envisioned that through the use of methods such as, but not limited to, tunneling, scattering, and the inclusion of vacuum gaps and other materials, will have the effect of generating propagating light. Where, it is contemplated that the near-field light may not be propagating until some mechanism is employed to facilitate propagation, such as tunneling, scattering, and leaky mode interactions. The source of the vibrations can be surface plasmon polaritons, surface phonon polaritons, localized surface plasmon resonance, molecular vibrations such as OH resonances from rotation and stretching etc., lattice vibrations, other various movements of charged particles, inter-band resonances, quantum confinement, quantum wells, quantum dots, rare-Earth transitions, clathrate compounds in which atoms or molecules exist in cage-like structures and have vibrational degree of freedom, and materials such as Heusler and Half-Heusler alloys, proton conductors, ion conductors, sorbents, zeolites, materials useful for thermoelectric conversion, etc. In addition, structuring thermally emissive materials can have an influence on the direction of the thermal emission and the spectral profile. Structuring may be accomplished in 0D, 1D, 2D, and 3D geometry, such as dots, multilayer stacks, surface corrugations, nanorods, photonic/phononic crystals, porous materials, gratings, etc. In addition, the inclusion of spacers made of vacuum or other materials which prevent or reduce the conduction of heat could be used to enhance the conversion of the thermal energy to electromagnetic radiation. Furthermore, it is envisioned that various combinations of the said methodologies and materials can be combined together to form one which improves the desired properties. Associated chemical changes in the environment interfere with the process of thermal-electromagnetic radiation including changes to the process or to the extent of the process, i.e., strength, frequency, direction, etc. It is this interference which is detected to determine chemical interaction changes. In the case of thermal energy harvesting, such as in thermophotovoltaics and thermoelectrics, this change can enhance the output thermal radiation or electric current, thereby enhancing the conversion efficiency of the system.

A relationship exists between the emissivity of a material and the absorptivity. This relationship is a measure of the radiative thermal emission of mass as compared to a blackbody for which the maximum amount of radiative thermal emission can be generated at a given temperature at equilibrium. Absorptivity is well known to be dictated by the optical and physical constants of a given material system, and the dependence of these constants on ambient environmental parameters has previously been exploited in optical-based sensors for a range of parameters of interest. For example, Au incorporated oxide materials have demonstrated a shift in a characteristic absorption peak associated with Au nanoparticles upon exposure to reducing or oxidizing conditions under elevated temperature conditions. The origin of this shift can be a modification to the refractive index of the oxide material and/or an effective charge transfer to and from Au nanoparticles. To monitor optical shifts associated with such materials, they are typically illuminated with an optical light source in a transmission, reflection, or optical fiber probe-based geometry to sample the optical properties of the material which are then monitored through an optical spectrometer or a photodetector. Thermal emission has also been exploited for temperature sensing in which the well-known temperature dependence of thermal emission is used to determine the temperature through monitoring the emitted light at a particular wavelength, the distribution of the emitted light, etc. For the practical operation of such method the emissivity of material is fixed, allowing the determination of the absolute temperature of the environment from the well-known Planck's law, describing thermal emission as a function of light frequency and environment temperature The method and apparatus described herein include monitoring changes in the electrical, physical, and/or chemical properties of a sensing material, from here on simply referred to as changes in the material, by taking advantage of the associated modifications to the thermal emissivity. In practice, the thermal emittance of a material can be measured through the normal optical detection schemes such as spectroscopy or photodetectors, etc. to monitor changes of a sensor material under investigation for the purpose of gaining information about chemical composition of a gas stream of interest. The method and apparatus do not require the utilization of a light source, and it is particularly effective when integrated with optical fiber based sensors due to the ability to collect a relatively large amount of thermally emitted radiation from a given functional sensor material with minimal interferences from the ambient thermal emission of the environment to be monitored.

Example embodiments of the emissive sensing materials falling within the scope of the method and apparatus are illustrated in FIGS. 1A-1F. In some embodiments, the thermally emitting sensing material may be utilized in particulate or nanoparticulate form as illustrated in FIGS. 1A-1C. The particulate thermal emitters 12 could be deposited directly on substrates 14 as shown in FIG. 1A, deposited on the underlayer 16 as shown in FIG. 1B, and embedded in a matrix material or phase 18 as shown in FIG. 1C. The exploitation of the underlayers 16 or matrix phase 18 can help to improve adhesion, increase high-temperature stability, and/or modify the effective optical/physical/electrical/thermal properties of the thermally emissive sensing materials 10. Overlayers can also be placed on the sensing materials and/or the sensing layers can be integrated into a multilayered stack for the purpose of optimizing the effective properties for compatibility with a particular optical sensing platform and/or for enhancing the selectivity of the optical response to a particular chemical species of interest. Thermally emissive sensing layers can also be utilized in the form of a monolithic or a porous film 20 deposited on the transparent substrate 14 as shown in FIG. 1D. FIG. 1E illustrates the particulate thermal emitters 12 incorporated in a multilayer stack, and FIG. 1F illustrates the particulate thermal emitters 12 under an overlayer. Once again, underlayers and overlayers as well as integration into multilayered stacks may be utilized to optimize the effective response. In addition, the thermally emissive sensing materials 10 and the particulate thermal emitters 12 may be embedded within multilayer thin film stacks to optimize their optical performance and/or high temperature and harsh environment stability. The thermally emissive material may be placed inside an optical cavity, which could be manufacture in a variety of ways, as is known in the art, such as through gratings, mirrors, notches, and etc. The cavity could alter the spectral profile of the emitted light and increase the magnitude of the light leaving the system, and when the system is well engineered a thermally driven laser could also be fabricated where some of the properties of the laser would be derived from changes in the emissive material due to environment interactions.

Note, Nicholas Karker et al. have recently described "thermal energy harvesting" by collecting ambient light from a high-temperature environment and directing it through a sensing layer using free-space optics (i.e., a mirror). This is described in Nicholas Karker et al., "Thermal Energy Harvesting Plasmonic Based Chemical Sensors," ACS nano, 2014—ACS Publications, VOL. 8, NO. 10, 10953-10962. In this work, Karker et al. intend to directly monitor absorptivity of the material, not emissivity as described herein. The direct monitoring of the thermal emission of a sensor material is not described or demonstrated in this prior work by Nicholas Karker et al.

Optical Fiber Sensor

Figure 2B:
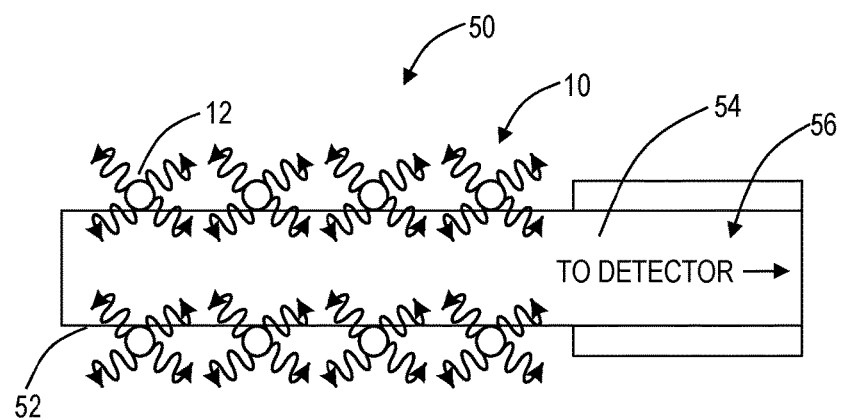

Referring to FIGS. 2A and 2B, in an exemplary embodiment, block diagrams illustrate a conventional evanescent wave absorption spectroscopy based optical fiber sensor 30 employing a light absorbing and/or scattering sensing material 32 and a light source 34 (FIG. 2A) as compared to an optical fiber sensor 50 exploiting the thermally emissive sensing materials 10 thereby eliminating the light source 34 (FIG. 2B). While the thermally emissive sensing materials 10 can be deposited on surfaces interrogated through standard free-space optics approaches, a particularly advantageous approach involves the coupling of the thermally emissive sensing materials 10 with an optical fiber-based (or other optical waveguide based) sensing platforms, such as the optical fiber sensor 50. An emissivity based sensing material can be coated on the end of an optical fiber, as well. Holes with various shapes may also be fabricated inside optical fibers which could be backfilled with emissive materials. An optical fiber may also be directly manufactured to have the desired emissive property. An optical fiber may also possess a device such as a fiber brag grating, a cavity, various other perturbations, and surface gratings which may be combined with other emissive components. It is contemplated that there exists a variety of methods to modify optical fiber, as is known in the art, which can interrupt thermal conduction/transport in favor of thermal radiation, such as any material discontinuity.

A common approach for monitoring changes in the optical properties of a sensing material through optical fiber based sensing approaches is illustrated in FIG. 2A in which the sensing material 32 is deposited on an exposed core 52 of an optical fiber 54 and the light transmission through the sensing region is monitored at a detector 56. This approach allows for direct monitoring of the real and imaginary parts of the optical constants of the sensing material 32 through the effective light absorption and/or scattering at the sensing element region and the effect of changes in the sensing material on the waveguiding properties of the fiber sensor device. In an exemplary embodiment, the optical fiber sensor 50 in FIG. 2B provides an approach that exploits the thermally emissive sensing materials 10. The thermally emissive sensing materials 10, i.e., the particulate thermal emitters 12, can be deposited on the exposed core 52 of the optical fiber 54. Here, the light source 34 is eliminated and the thermally emitted radiation of the particulate thermal emitters 12 is monitored directly by the detector 56.

The optical fiber sensor 50 enables modification of conventional evanescent wave absorption spectroscopy based optical fiber sensors 30 to operate without the need for external probing with a light source 34. The optical fiber sensor 50 provides dramatically reduced cost, increased simplicity, and new functionality. Also, the optical fiber sensor 50 provides the ability to monitor both sides of a "transmission" based evanescent sensor simultaneously to derive unique information (spectral wavelengths, spatially localized information, etc.). That is, the optical fiber 54 can include another detector 56 on opposite end of the optical fiber 54 from the detector 56 illustrated in FIG. 2B. In another exemplary embodiment, the optical fiber 54 itself can include the particulate thermal emitters 12 such that the optical fiber 54 itself may be changing as a result of the chemical constituents of the surrounding environment. In this embodiment, there is no need to deposit the particulate thermal emitters 12 on the exposed core 52 of the optical fiber 54. It is also contemplated where monolithic emitters in the sensing layer or the optical fiber core material do not have thermal emitting particulates but do have an inherent emission and can be composed of materials whose properties changes due to environmental changes. In some cases, thermal emitters can be created within a sensing layer, core material, or cladding material through processing to introduce additional emission not present prior to the processing steps. Through spatially localized processing techniques, such emitters can also potentially introduce spatially localized emission based sensor elements for chemical sensing and chemical spectroscopy. Spatially localized processing, when nanostructured and/or structured on the order of the wavelength of monitored electromagnetic radiation, can also result in tuning of the spectral emission profile as well as the directivity, as is known in the art.

Thermally Emissive Sensing Materials in Optical Fiber Sensors

Figure 3:
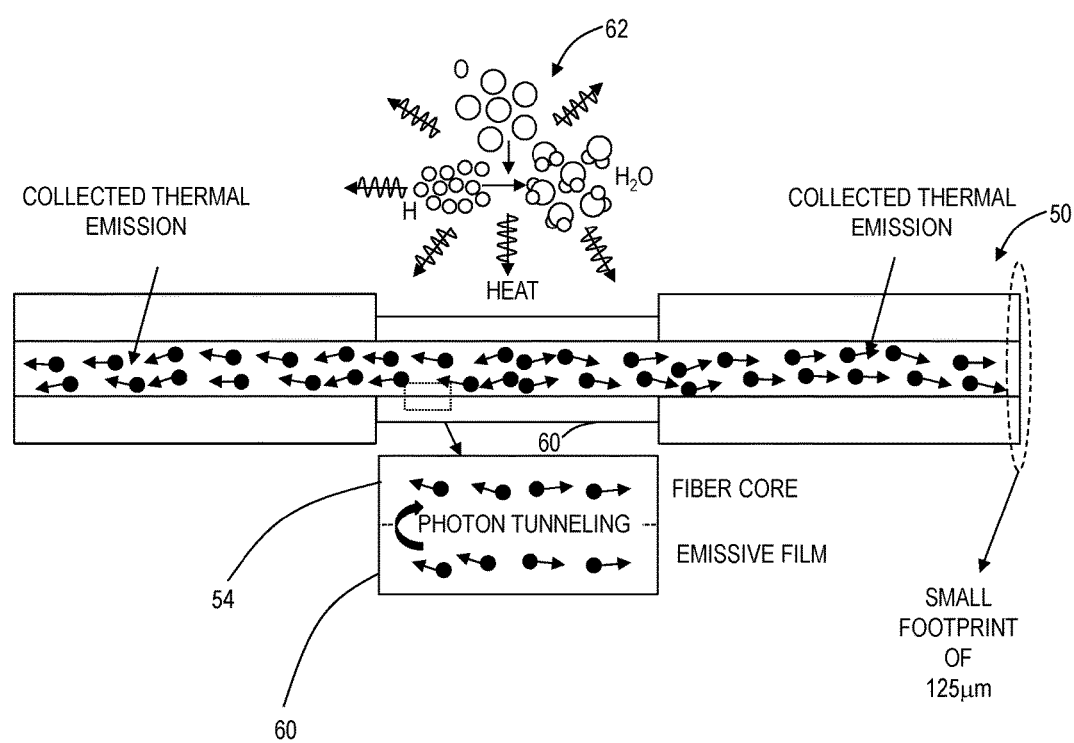
FIG. 3 is an exemplary diagram that illustrates the general operating principles of thermally emissive sensing materials integrated with optical fiber.

Referring to FIG. 3, in an exemplary embodiment, a schematic diagram illustrates general operating principles of the thermally emissive sensing materials 10 in the optical fiber sensor 50. In this exemplary diagram, photon tunneling is depicted as the coupling mechanism of thermally emitted light into the core of the optical fiber. In addition to tunneling, other mechanisms such as, but not limited to, direct emission into the core and scattering may be utilized although in many cases tunneling may be a preferred embodiment for a combination of high coupling efficiency and isolation from background electromagnetic radiation. Here, the optical fiber sensor 50 includes an emissive film 60 deposited on the optical fiber 54 core. The emissive film 60 can include one of the thermally emissive sensing materials 10, such as in FIG. 1. The presented configuration has an emissivity collection enhancement benefit in comparison with other free space counterparts. In other words, by placing the emissive film 60 on the optical fiber 54, the light collection efficiency can be increased and is mediated by evanescent interactions. In non-structured materials ("structured materials" referring to surface relief gratings, photonic/phononic crystals, carbon nanotubes, fiber Bragg gratings, etc.) generally there is not a preferred direction to thermal emission. When coated on the optical fiber 54, light within the acceptance cone of the optical fiber 54 is collected across the thermally emissive coating length of the emissive film 60. The emissive film 60 can be a thin film coating on the order of ~100 nm (or larger, including up to 20 times the size, such as several micrometers, or smaller such as a <100 nm), where the thickness of the film facilitates the coupling of the emitted thermal radiation into the many electromagnetic (EM) modes inside the optical fiber 54 core, potentially through tunneling, scattering and leaky mode interactions, for the efficient collection with isolation from background thermal light. By this type of a configuration, thermal radiation can be directly coupled into guided modes inside the optical fiber 54 and allows the optical fiber 54 to extract the thermal radiation of the emissive film 60 with minimal environmental interference. Emissivity based chemical sensing/spectroscopy has not been demonstrated in a free space configuration either and some form of free space based optical monitoring of an emissivity sensing material could also be used for environmental composition monitoring such as through imaging spectroscopy. Although free space methods can offer the advantages of monitoring chemistry over a wide area surface, they require optical access to be effective and background thermal emission could be much stronger relative to the thin film radiation due simply to geometric and optical considerations. As a result, optical fiber based sensor configurations are advantageous and preferred in many applications where background thermal emission is significant and free space optical access is not possible or convenient. Again, note the present disclosure is focused on directly monitoring emissivity through the thermal emission generated by the sensing material, not absorptivity. It is also envisioned that a configuration in which the described emissive materials can also be placed on an end-face of an optical fiber, in which case the light emitted by the coating will be captured by the optical fiber.

The optical fiber-based implementation partly relies on near-field thermal radiation of the emissivity based sensing material coupled to the far-field by coupling to waveguide modes in an evanescent configuration due to k-vector matching that inherently exists to support such a coupling mechanism, especially in a heavily multimode fiber having thousands of modes, and also potentially through leaky mode interaction and scattering. This evanescent based coupling approach is in contrast to measuring the near-field thermal emission by placing a scattering source in the near-field such as a tungsten tip, nanoparticles or by other techniques such as scanning near-field optical microscopy (SNOM) in analyzing the local electromagnetic density of states.

In the present disclosure, the surprising discovery is presented that significant changes can be induced in the thermal emissivity of a thin emissive film 60 integrated with the optical fiber 54 in the evanescent configuration due to changes in the chemical composition of its environment. Modifications to the electrical, physical, and chemical properties of the emissive materials, associated with interactions between chemical species and the sensing material, are responsible for the observed changes in the spectral profile and/or the magnitude of the emissivity. To this end, the method and apparatus include an exemplary hydrogen sensor powered solely by thermal energy and, due to its small geometric footprint (~100 μm), it should only weakly perturb most environments. The presented results show clear evidence of chemical composition analysis in harsh high-temperature conditions by the in-situ monitoring of the hydrogen composition at temperatures of 800° C. The presented configuration, in which the emissive film 60 is integrated with the optical fiber 54, provides an unmatched opportunity for fast in-situ thermal emissivity based chemical composition monitoring due to its high collection efficiency of thermally radiated light and its inherent ability to isolate the collected sensory information from sources of interference. The presented paradigm should provide a new route of sensor exploration for high-temperature harsh environments with a wide impact in energy generation systems, chemical plants, and other high-temperature processes.

Optical Fiber Sensor Configurations

Figure 4A:
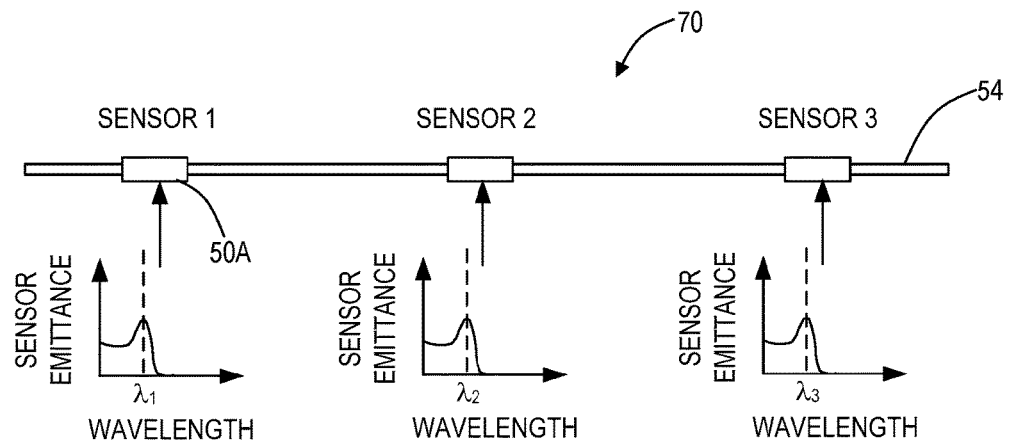
FIGS. 4A-4C are block diagrams of optical fiber sensor configurations including multiple optical fiber sensors in a single optical fiber (FIG. 4A), multiple optical fiber sensors with Fiber Bragg Gratings (FBG) (FIG. 4B), and multiple optical fiber sensors in a bundled fiber (FIG. 4C).
Figure 4B:
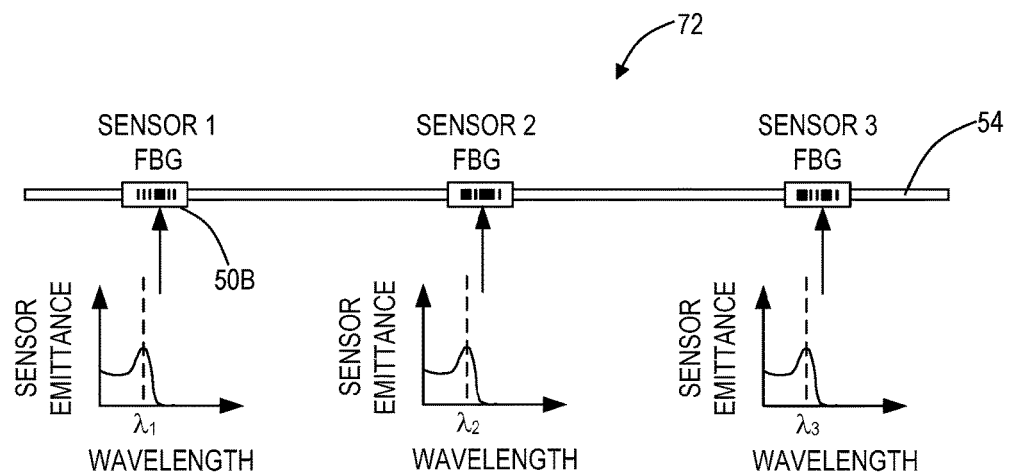
Figure 4C:
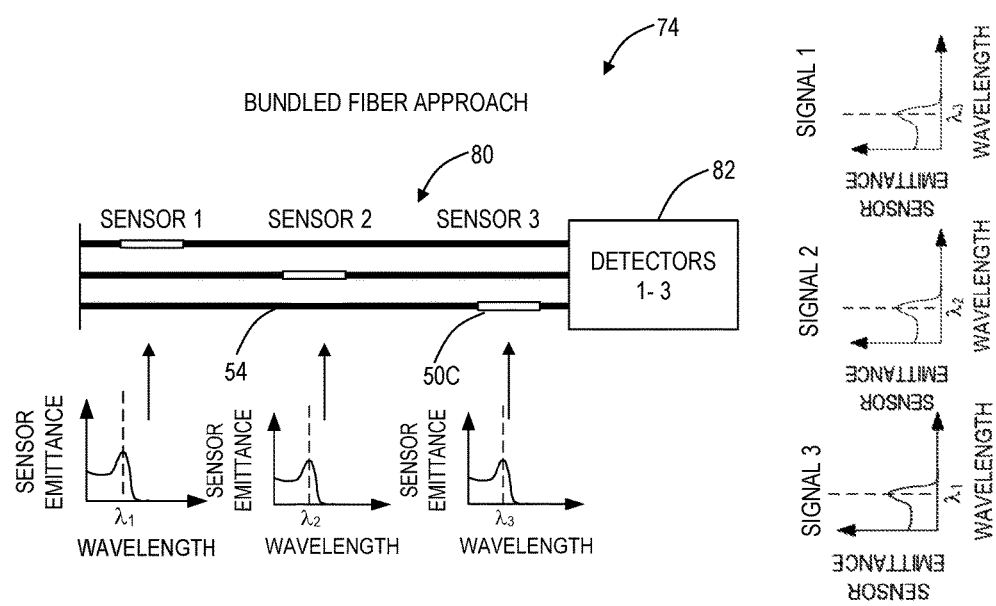

Referring to FIGS. 4A-4C, in an exemplary embodiment, block diagrams illustrate optical fiber sensor configurations 70, 72, 74, including multiple optical fiber sensors 50A in a single optical fiber 54 (FIG. 4A), multiple optical fiber sensors 50B with Fiber Bragg Gratings (FBG) (FIG. 4B), and multiple optical fiber sensors 50C in a bundled fiber 80 (FIG. 4C). Specifically, the optical fiber sensor configurations 70, 72, 74 can provide distributed interrogation through spatial and/or wavelength localization. The optical fiber sensor configurations 70, 72, 74 support the optical fiber sensors 50A, 50B, 50C as multiple sensing elements to enable distributed sensing capabilities. For example, both ends of the optical fiber 54 can be monitored at the same time. This provides the ability to get information about spatial location The optical fiber sensor configurations 70, 72 include a single optical fiber 54 with the optical fiber sensors 50A, 50B distributed thereon. The optical fiber sensors 50A can be similar to the optical fiber sensor 50 with the thermally emissive sensing materials 10, i.e., the particulate thermal emitters 12, deposited on the exposed core 52 of the optical fiber 54. The optical fiber sensors 50B can be similar, but are also integrated with a Fiber Bragg Grating (FBG). The FBG is just an example of a fiber modification that could be used herein; other embodiments are also contemplated, such as surface corrugations, holes and other shaped structured drilled and/or milled into the fiber. In some cases, the core and/or cladding may comprise the thermally emitting sensing material which can be spatially varied allow for spatial localization and/or spectral tunability of the emission profile. FIG. 4C illustrates the bundled fiber 80 coupled to multiple detectors 82. The bundled fiber 80 includes multiple optical fibers 54, each with one of the optical fiber sensors 50C. Other configurations are also contemplated.

Figure 5:
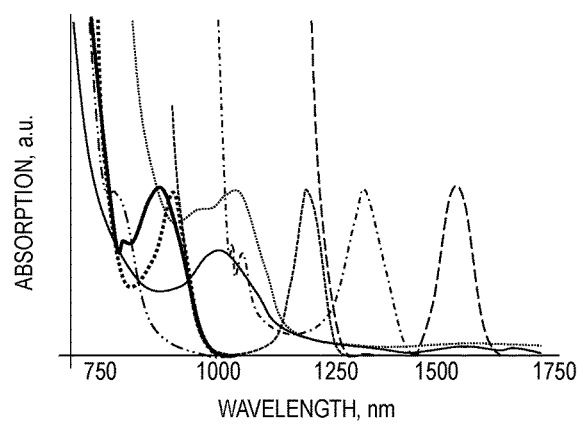
FIG. 5 is a block diagram and a graph of additional details of the optical fiber sensor configurations showing the single fiber configuration acting as a linear combination of the optical fiber sensors. Note that although the thermal emission based sensing elements are illustrated as films on the core of the optical fiber, in some embodiments the thermal emission based sensing element can be comprised within the core of the optical fiber.
Figure 5:
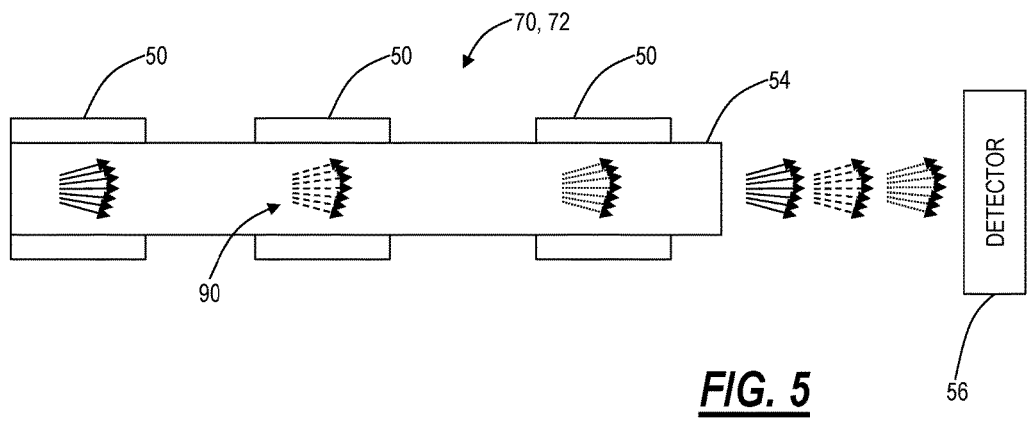

Referring to FIG. 5, in an exemplary embodiment, a block diagram and a graph illustrate additional details of the optical fiber sensor configurations 70, 72, showing the single fiber configuration acting as a linear combination of the optical fiber sensors 50. Here, each of the sensors 50 sends associated signals 90 to the detector 56. Each of the optical fiber sensors 50 is adapted, i.e., configured with associated thermally emissive sensing materials 10 which have spectrally identifiable features and can be isolated by some technique known in the art.

Optical Fiber Based Energy Harvesting

Figure 6:
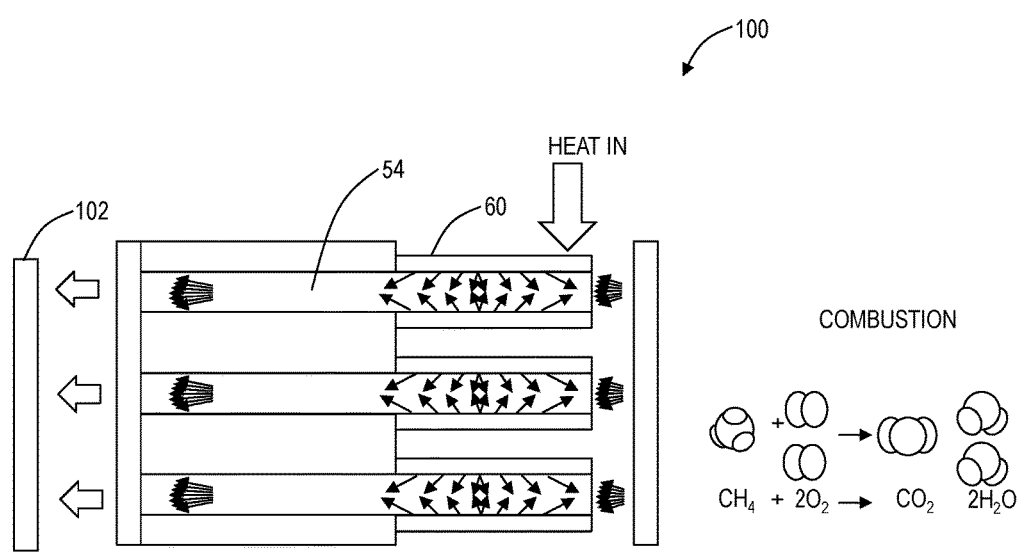
FIG. 6 is a schematic diagram that illustrates an optical fiber based thermal energy harvesting system including an optical fiber stack engineered to maximized thermal light collection into an optical fiber bundle from a heat source such as combustion, for example.

Referring to FIG. 6, in an exemplary embodiment, a schematic diagram illustrates an optical fiber based thermal energy harvesting system 100. Besides applications in the optical fiber sensor 50, the thermally emissive sensing materials 10 could also be used to convert and extract thermal energy which is converted to light and propagated away in the optical fiber or fibers, which can be converted to other forms of energy such as electrical energy when placed in tandem with a photovoltaic cell 102 or another type of photon to electrical energy conversion device, at an arbitrary distance away from the heat source. The light in the fiber bundle is then sent an arbitrary distance away from the hot-zone and converted into other useful energy, such as electricity using photovoltaic cells potentially coupled with filters. If present, the filters can act to restrict non-optimal light wavelengths from interacting with the photovoltaic cell, where the non-preferred wavelengths can be returned to and be recycled by the hot-zone. Environmentally/chemically induced emissivity variations can be used to monitor the chemical composition of the environment but can also help to improve upon the conversion of thermal energy into light, or thermal energy into an increase in free electron density/mobility etc., simply electrical properties, which could be extracted or can further be converted into light. For example, changing the chemical composition of the environment to one containing an optimal composition of hydrogen with other gasses can act to increase the thermally emitted light, which may be useful in thermophotovoltaics, in conjunction with sensing and spectroscopy. Given that the environment induced changes alter the materials chemical, physical, or electrical properties, Thermoelectric systems could also see an efficiency enhancement by changing the environment for some or all portion of the system. The thermally emissive material could be in the presence of chemical reactions or could facilitate chemical reactions whose product can be that which enhances the thermally emitted light, or the free electron density/mobility, which may be heat, charge transference, radical formation, chemical identity change, a variety of surface interaction, and etc. When fiber is used, the carried away heat in the fiber does not need to be converted and may also serve the function of heat transfer or heat conduction away from a place desired to be cooled or a place desired to be heated remotely from the heat source. However, converting the light in the fiber to electricity would provide the added benefit of energy recovery in application where it makes sense.

A variety of configurations could be explored with the goal of optimizing the conversion/collection of thermal energy by the optical fiber 54. In one realization the ends of the optical fiber 54 could be modified by replacing the cladding material with one that maximizes thermal emission/near-field thermal coupling to guided modes inside the fiber core along with maximizing the collected light by the end-face of the fiber, which may also involve some of the described methodologies, to obtain a combined thermal energy to collected light conversion and extraction maximum. In essence, any of the modifications suggested for emissivity based sensing/spectroscopy, some of which is outlined herein, is also envisioned to provide material choices and methodologies applicable here, as well. Then, individual fibers could be stacked to form a bundle, block, or brick with or without other optimizing material constituents. The hot side of the fiber would collect/convert thermal energy into light. The colder side of the fiber/fiber-stack could be combined with a filter, which could easily be fabricated through standard techniques such as sputtering, sol-gel deposition, spray coating, etc., only to allow photovoltaic (PV)-cell preferred light to pass through, returning other wavelengths back to the thermal source for recycling. Where, the filter component is deemed as an optimizing component in some cases, not a necessary one for thermal energy extraction. A PV cell could also be directly integrated into the fiber in the end-coating configuration or as a side coating which would interact either through evanescence, through leaky modes, or through scattering. An optical fiber that has been optimized for collecting/converting thermal energy into light in the desired wavelength range could find uses in other areas, as well. For example, one could seek to apply the concept for enhanced thermal conduction without the presence of corresponding electrical conduction through light extraction and transport. In contrast, more conventional thermal conductors such as an equivalent dimension of copper wire will typically also display a large electronic conductivity that can be disadvantageous in the case of electrified systems and would leak heat throughout, whereas guided heat in the form of electromagnetic radiation can be engineered to have very little leaky losses. This type of geometry can also potentially be optimized to harvest near-field thermal radiation which has been recently shown to be larger than predictions of far-field blackbody thermal radiation by orders of magnitude. In one embodiment, the specialty nanomaterial coating would harvest nearby thermal energy and convert it to guided light in the fiber by coupling the strong near-field radiation into guided modes, in addition to or in conjunction with scattering and leaky mode interactions. The hot end face of the fiber could be placed at an optimal distance from a thermal emitter to harvest thermal energy. Then, individual fibers could be combined into a block or a brick and combined with filtering and photovoltaic cells.

Example Embodiments: Doped Metal Oxide Sensing Layers

A number of metal oxide based films were explored for the emissive film 60 to examine their thermal emission properties in varying hydrogen high-temperature environment. Standard silica based (125 μm) multimode optical fiber 54 with fluorine doped cladding and a core size of ~105 μm was modified by removing the 20 μm cladding material for a 3 cm approximate length of fiber using buffered hydrofluoric acid (Hf) etching. The emissive films 60 were coated on the optical fiber 54 by generating a droplet of the prepared coating solution using a micropipette and dragging it across the modified length of optical fiber 54. Several coatings may be applied successively to increase the desired film thickness. The typically coated film thicknesses are on the order of ~100 nm. The as prepared optical fibers 54 were then annealed in a high-temperature furnace in an air atmosphere at temperatures from 800° to 950° C. The emissivity of the thin-film-coated fibers were measured in the same furnace by adjusting the temperature to 800° C. and replacing the air atmosphere with controlled amounts of nitrogen, hydrogen, and oxygen. A halogen light source was coupled to the modified fiber to illuminate the sensor element, and the transmitted spectra were measured with spectrometers. That is, standard interrogation using a light source in both the visible and near-IR wavelength ranges was performed to demonstrate the nature of the sensing element under study. Subsequently, the light source was eliminated, and the thermally emitted light was directly monitored during identical sensing test exposures.

The method and apparatus described herein report highly effective thermal emission based chemical sensing at temperatures as low as 800° C. by observing thin-film emissivity changes due to environmental chemical composition changes. Specifically, the present disclosure shows that incorporating sensory films with optical fiber in the evanescent wave configuration is especially well suited for thermal emission based spectroscopy. The placement of sensory thin-films in the strong evanescent tunneling region of optical fiber preferentially couples the emitted light of the film with an exponential radial probability distribution moving away from the fiber core. This coupling mechanism along with conventional thermal transfer/radiation is believed to be the source of the observed effect. In comparison with other techniques, this configuration should provide a relatively high signal isolation and high signal to noise ratio.

Exemplary results show the variations in the measured optical signals as a function of wavelength for varying hydrogen concentrations from 5% to 98%. Additional developments are possible by incorporating the many detailed techniques for thermal radiation tailoring from free carrier doping, doping by rare earth atoms, the inclusion of quantum dots, including polar interfaces to enhance the EM density of states, by interrupting thermal conduction at the film-fiber interface to preferentially enhance thermal radiation, employing ionic/proton conductors to selectively interact with chemical species, and so on. The present disclosure provides a new paradigm for sensor design and exploration with wide impact in a variety of energy generation and other high-temperature processes. The finding may also provide new insight into methods for thermal PV-based approaches that exploit the unique optics and geometry of the fiber optic sensing platform to overcome prior challenges associated with free space coupling while also potentially leveraging new and exciting work in near-field enhanced thermal emission being reported in the literature.

Example Embodiments: Binary Metal Oxide and Metal Nanoparticle Incorporated Oxide Sensing Layers Explored techniques known to affect thermal emission and thermal spectra are micro/nanostructuring, doping with rare earth elements, quantum size effects, and through modifying the EM density of states with surface waves in polar/metallic materials and metal nano-particles which supply narrowband resonances. In addition to these approaches used for thermal emissivity/spectra tailoring, the thermal emission of the thermally emissive sensing materials 10 and the emissive film 60 can be drastically altered with environmental chemistry and this altered emission can be observed with high isolation with the optical fiber 54 through near-field evanescent tunneling. With the presented paradigm, material systems can be characterized with interesting optical properties such as for the result of the thermal excitation of localized surface plasmon activity of a Pd-nanoparticle $TiO_2$ system, as a function of $PH_2$ at 1073 K in the Ultraviolet (UV)-Visual (Vis) range. The extraction of thin-film emission with high isolation from the thermal background is foreseen to pave the way for developments in thermal based spectroscopic techniques.

Various thermal spectrum monitoring configurations have been described herein, in which the thermally emissive sensing materials 10 and the emissive film 60 is brought into the tunneling region of the optical fiber 54, powered solely by thermal energy and having a geometric footprint of ~125 μm, is of profound simplicity, providing a new method for in-situ chemical spectroscopic analysis with an impact in energy generation systems and other high temperature chemical processes, such as in solid oxide fuel cells. There is a definite lack of methods for fast in-situ chemical composition analysis at temperatures above 700 K due to various failure mechanisms in the conventional approaches, prompting the exploration of optical fiber as a viable alternative and making the breakthrough results presented here of widespread significance and importance.

Rytov's theory of fluctuational electrodynamics brought new insights to thermal physics as it predicted the thermal near-field, with evanescent emissions orders of magnitude greater than that predicted by Planck's far-field theory. Thermal fluctuations in the motions of charged particles are present in all matter, producing currents that can excite optical decay channels, such as surface phonon/plasmon polaritons with strong evanescent thermal emissions. Silica and silicon carbide are explored materials owing to their polar structure, supporting surface phonon polaritons. In heavily doped silicon nanoscale evanescent exchange coupling is predicted to yield an astonishing five orders of magnitude increase in the radiative flux, relative to Planck's far-field prediction, due to the large EM density of surface states. In addition, in thin films with thicknesses comparable to the optical penetration depth, the entire volume can contribute by increasing the photon lifetime and through other mechanisms such as delocalized surface waves.

In conventional experimentation, measurement of the evanescent thermal near-field is achieved by scattering into the far-field for observation. In contrast, optical fibers 54 can provide rich tunneling possibilities for surface and in volume thermal excitations due to high guided EM mode densities and can transmit the collected light with low losses to spectrometers (detectors 56) at remote locations. Extraction through evanescent tunneling inherently provides isolation from the large thermal background. An approach that collects and guides ambient thermally emitted light, to eliminate the need for a light source 36, for subsequent transmission based measurements of environmentally induced resonance shifts in plasmonic composite films on planar substrates, has been demonstrated recently by prior authors. The present disclosure represents a dramatic advancement beyond this previously demonstrated concept by also eliminating the need for additional free-space optics through direct interrogation of thin-film near-field emissivity.

Figure 7A:
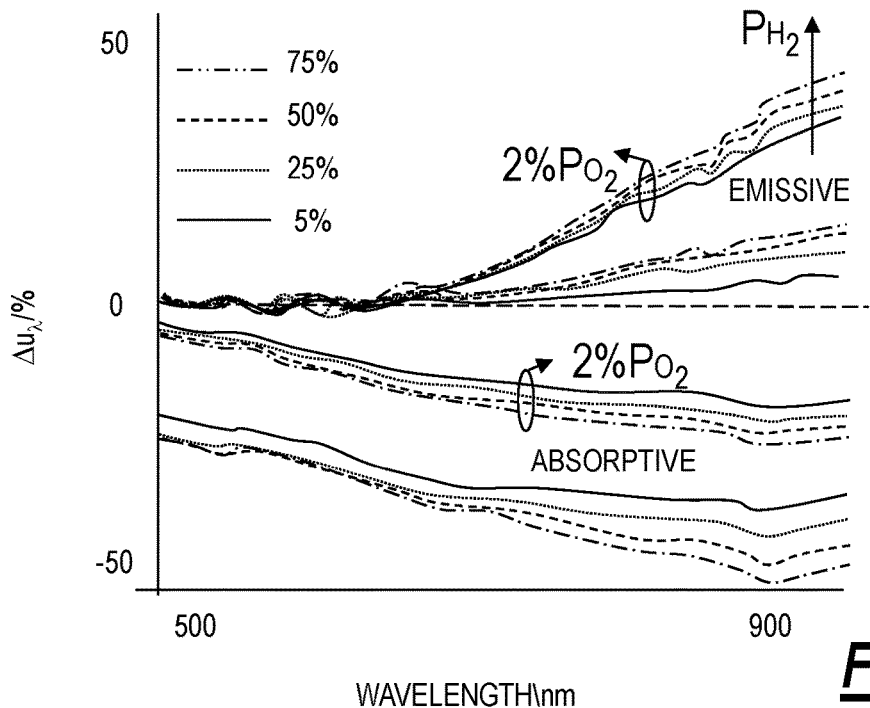
FIGS. 7A-7B are graphs of relative spectral energy density changes ($\Delta u_\lambda = [u_{o,\lambda} - u_\lambda]/u_{o,\lambda}$) in the UV-Vis range in $P_{H2}$ of 0-75% for $TiO_2$ (FIG. 7A) and Pd—$TiO_2$ (FIG. 7B) with $N_2$ balancing.
Figure 7B:
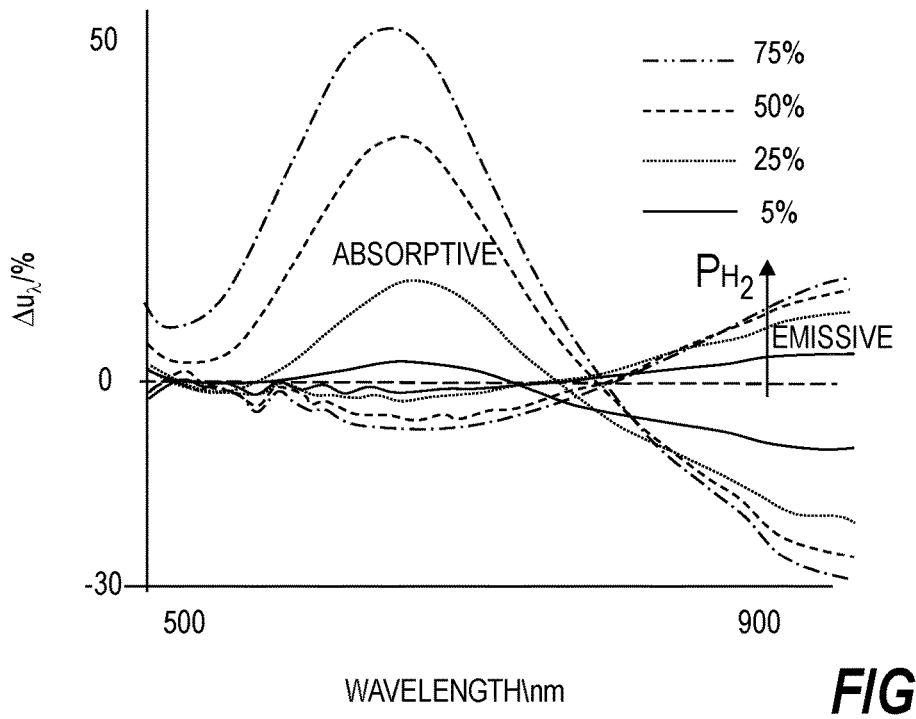

To further demonstrate additional embodiments of the invention disclosed, additional experiments are presented for binary metal oxide and metal nanoparticle incorporated metal oxide films as described in more detail below. Referring to FIGS. 7A-7B, in an exemplary embodiment, graphs illustrate relative spectral energy density change ($\Delta u_\lambda = [u_{o,\lambda} - u_\lambda]/u_{o,\lambda}$) in the UV-Vis range in $P_{H2}$ of 0-75% for $TiO_2$ (FIG. 7A) and Pd—$TiO_2$ (FIG. 7B) with $N_2$ balancing. Different curves are indicated for emission measurements relative to absorptive where measurements are performed under illumination. The interaction was recorded when the thin film was probed with an external halogen light source (absorptive), and by measuring thermals emission (emissive) only. FIG. 7B is a plot of the interaction of a $TiO_2$ thin-film containing palladium nanoparticles with visible light, with and without external illumination. The important feature of this figure is the plasmonic activity of the composite and that this plasmonic activity can be excited by the thermal energy and that the plasmonic activity of the composite is a function of the chemical composition of the environment. The foregoing presents results showing considerable changes in the emissivity of the emissive film 60 due to changes in the environment $P_{H2}$. This is demonstrated with $TiO_2$, Pd—$TiO_2$, and Au—$TiO_2$ nanocomposites, with varied properties from high conductivity, hydrogen absorptivity, and localized surface plasmon resonance (LSPR) based activity in nitrogen and in an oxygen-containing high temperature (1073 K) environments. The thin-film emission of $TiO_2$ was observed with relative ease (positive y-axis of FIG. 7A) in the UV-Vis range, indicating the benefit of the proposed configuration to monitor otherwise weak thermal excitations (blackbody thermal emission peak at 2.7 μm at 1073 K) with high isolation. The relative change in the spectral energy density ($\Delta u_\lambda = [u_{o,\lambda} - u_\lambda]/u_{o,\lambda}$) is shown for $P_{H2}$ of 0 to 75% in nitrogen. In conjunction with emission based measurements, the absorptive response of the films 60 was collected for direct comparison. A strong wavelength-dependent absorption is observed when probed with an external light source, with an illumination spectral energy density several orders of magnitude larger than thermal emission. The various factors that may influence the observed spectra include free electron absorption, Burstein-Moss shifts of the band-edge, and film thickness based interference effects. The measured absorptive and emissive data are of similar shape and of opposite sign, as expected based on simple arguments from Kirchoff's theory. However, further characterization is needed to quantify the mechanisms, including the near-field contributions from in volume and from the two interfaces.

Figure 8:
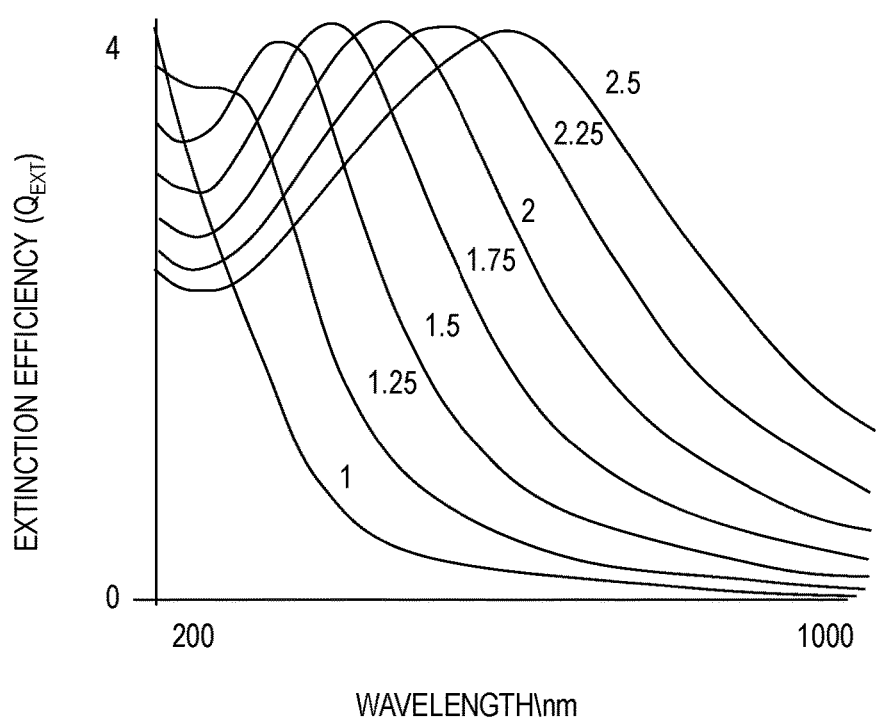
FIG. 8 is a graph of Mie scattering calculations performed for 50 nm size Pd nanoparticles embedded in a dielectric background.

In the case of the Pd—$TiO_2$ system, Pd-nanoparticles disassociate $H_2$, which then diffuses into Pd occupying lattice sites, promoting charge transference due to a reduction in the work function accompanied by changes in the electronic band structure. The wavelength localized features in absorption based measurements in the UV-Vis are asserted to be LSPR based upon Mie scattering calculations (FIG. 8), blue shifted and increasing in magnitude with $P_{H2}$ (FIG. 7B). This means the peak is red-shifted and/or decreasing in magnitude. Specifically, FIG. 8 illustrates a graph Mie scattering calculations performed for 50 nm size Pd nanoparticles embedded in a dielectric background. FIG. 8 describes that the observed wavelength dependence of the Pd—$TiO_2$ nanocomposite at visible light wavelength is plasmonic-based in origin; given that the LSPR resonance of the Pd nanoparticles is in the right wavelength range for the particular particle size and the expected refractive index of the material host, which in this case is $TiO_2$. The refractive index of the dielectric background was varied between 1 and 2.5, to explore the displacement in the localized surface plasmon resonance (LSPR) peak. Scanning electron microscopy demonstrates that the Pd nanoparticles are ~50 nm, a particle size for which LSPR activity has been explored. Furthermore, this activity is thermally excitable in the UV-Vis as a function of $P_{H2}$ and this should be the first observation of thermal excitation of such a mechanism in this wavelength range. As in the case of the $TiO_2$ film, the shape of the response at higher wavelengths appears to be dominated by free-electron absorption in the $TiO_2$ matrix phase, and the measured emission mirrors this shape.

Figure 9:
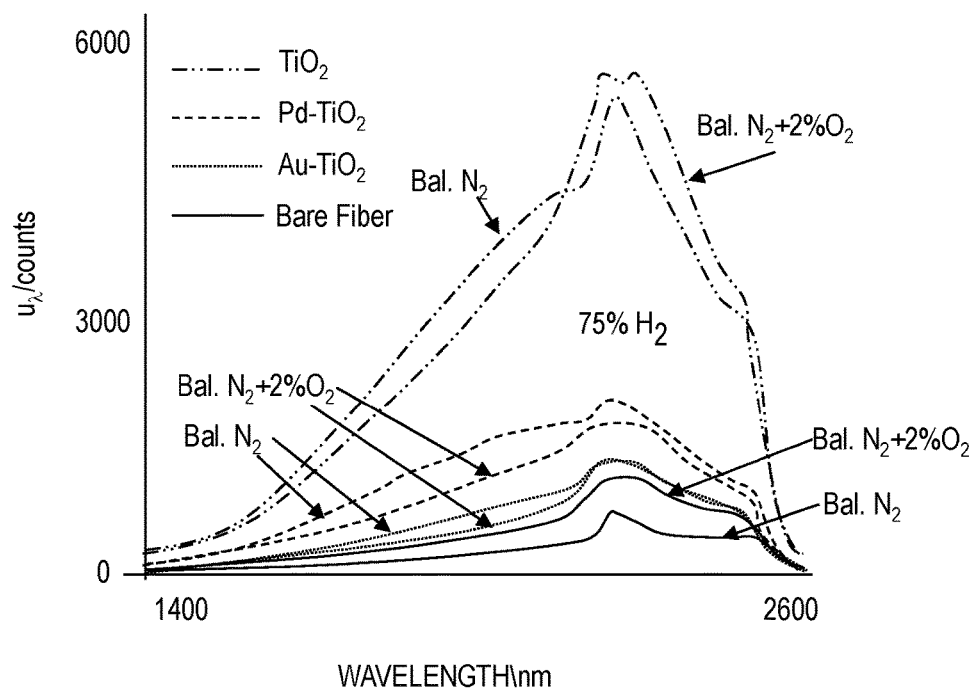
FIG. 9 is a graph of a thermal emission (spectral energy density $u_\lambda$) comparison of bare fiber, and thin films of $TiO_2$, an Au—$TiO_2$ nanocomposite, and a Pd—$TiO_2$ nanocomposite in $P_{H2}$ of 75% balanced with $N_2$ and with 2% $O_2$.

Referring to FIG. 9, in an exemplary embodiment, a graph illustrates a thermal emission (spectral energy density $u_\lambda$) comparison of bare fiber, and thin films of $TiO_2$, an Au—$TiO_2$ nanocomposite, and a Pd—$TiO_2$ nanocomposite in $P_{H2}$ of 75% balanced with $N_2$ and with 2% $O_2$. The measured thermal emission of the various thin emissive films 60 is shown in FIG. 9, for the NIR wavelength range. The $TiO_2$-film has the highest thermal emission, which is attributed to a higher free electron concentration and mobility brought on by mechanisms such as grain barrier potential height reduction, oxygen vacancy concentration, and, potentially, by the creation of interstitial Ti. The incorporation of Au and Pd nanoparticles supply exploitable mechanisms such as LSPR and $H_2$ selective interactions, but may also potentially function as scattering centers and charge depletion regions. An $O_2$ partial pressure reduces the magnitude of thermal emission, except around the silica O—H vibrational resonance wavelength of 2247.19 nm. At these temperatures, $O_2$ and $H_2$ can result in the formation of additional hydroxyls defects within the silica core, supplying thermally excitable resonances that can also impact the measured sensing responses for emission based chemical spectroscopy.

Figure 10A:
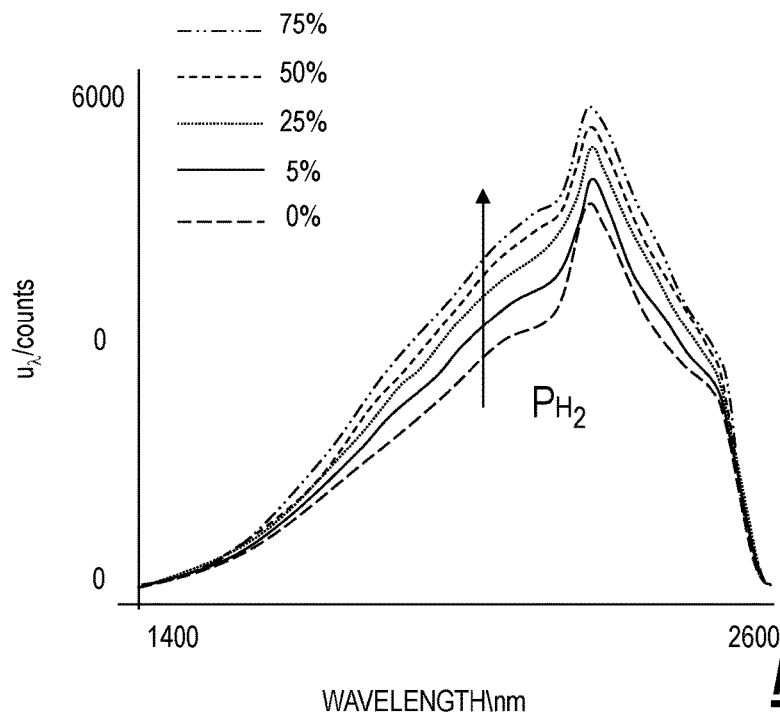
FIGS. 10A-10B are graphs that illustrate measured emitted spectral energy density ($u_\lambda$) at NIR wavelengths for the $TiO_2$-film in $P_{H2}$ of 0-75%, with $N_2$ balancing (FIG. 10A) and relative spectral energy density change ($\Delta u_\lambda = [u_{o,\lambda} - u_\lambda]/u_{o,\lambda}$) of the films in $P_{H2}$ of 75%, relative to 0%, with $N_2$ balancing and with a $P_{O2}$ of 2% (FIG. 10B) for both emissive and absorptive based responses.
Figure 10B:
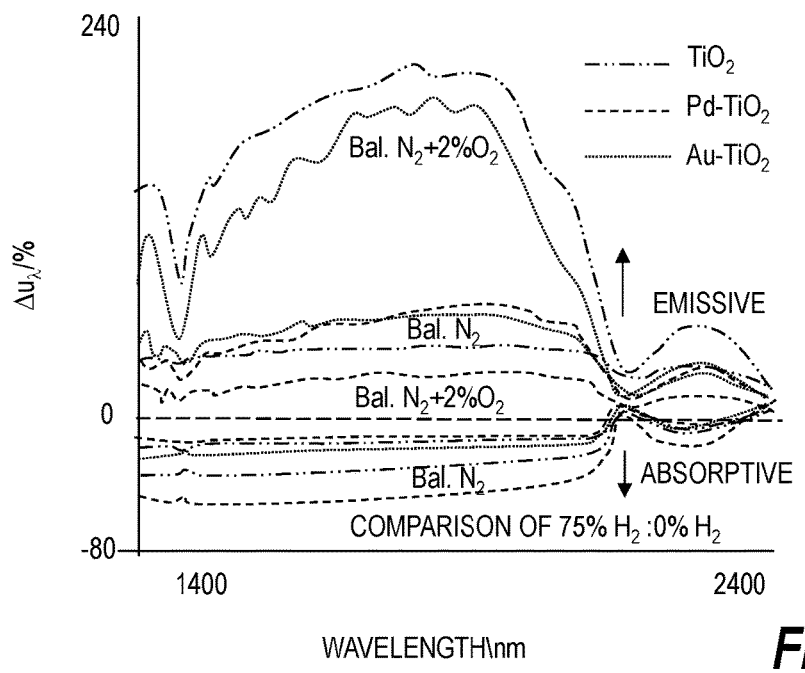

Referring to FIGS. 10A-10B, in an exemplary embodiment, graphs illustrate measured spectral energy density ($u_\lambda$) at NIR wavelengths for the $TiO_2$-film in $P_{H2}$ of 0-75%, with $N_2$ balancing in FIG. 10A and relative spectral energy density change ($\Delta u_\lambda = [u_{o,\lambda} - u_\lambda]/u_{o,\lambda}$) of the films in $P_{H2}$ of 75%, relative to 0%, with $N_2$ balancing (emissive) and with a $P_{O2}$ of 2% (absorptive) in FIG. 10B. Besides the increase in overall emission and changes in the emitted light induced by chemical composition changes, another important observation in the relative strength of the hydroxyl vibration (strong peaks in the data). Incrementally increasing $P_{H2}$ provides a corresponding emissions increase (FIG. 10A), for the $TiO_2$-film, with a relative spectral energy density change of 210% (positive y-axis of FIG. 10B). The second largest emissive change is observed for Au—$TiO_2$ and is approaching 200% with a $P_{H2}$ of 75%. The Pd and Au systems have a comparable increase in comparison with base $TiO_2$ in $N_2$. A $P_{O2}$ of 2% provides a substantial increase in the measured thermal emissions except for the Pd-system in which the presence of oxygen prompts the competition between $H_2$ disassociation/chemisorption and oxidation/catalysis, where the latter appears to dampen thermal emission. In contrast, Au nanoparticles are well known to have enhanced resistance to oxidation. With $N_2$ balancing, the measured emissivity and absorptivity changes are comparable in magnitude, as according to Kirchoff's law emissivity must equal absorptivity ($\varepsilon_\lambda = \alpha_\lambda$) in thermal equilibrium, for the conservation of energy to hold. Although, thermal equilibrium is not strictly satisfied here since thermal energy is removed through tunneling into the optical fiber and the near-field contributions must be accounted for, as well. The spectral data were collected after allowing the $P_{H2}$ induced transients to settle to the new steady state of operation in the thin-films, for which 30 minutes was allotted and were determined to be more than sufficient. Additional experiments were performed to rule out thermal conductivity based changes in the environment as being the source of the observations by (1) observing similar emissivity changes in the other reducing gases (e.g., CO) that do not have high thermal conductivities and (2) by the manufacture of an $H_2$ insensitive thin-film with very high overall thermal emission. These additional experiments clearly demonstrate that the measured sensing responses here are attributed to modifications to the chemical sensing layer emissivity in response to changing chemistry of the surrounding gas atmosphere.

Figure 11:
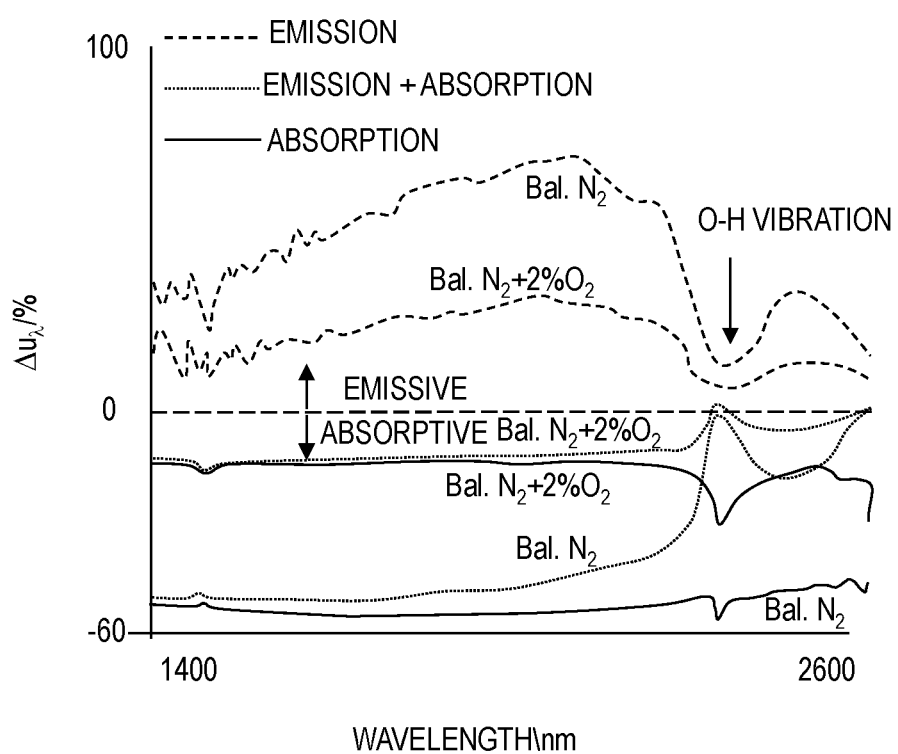
FIG. 11 is a graph that illustrates relative spectral energy density change ($\Delta u_\lambda = [u_{o,\lambda} - u_\lambda]/u_{o,\lambda}$) of the Pd—$TiO_2$ system in $P_{H2}$ of 75%, relative to 0%, with N2 balancing and with a $P_{O2}$ of 2% for both emissive and absorptive based responses.

Referring to FIG. 11, in an exemplary embodiment, a graph illustrates relative spectral energy density change ($\Delta u_\lambda = [u_{o,\lambda} - u_\lambda]/u_{o,\lambda}$) of the Pd—$TiO_2$ system in $P_{H2}$ of 75%, relative to 0%, with N2 balancing and with a $P_{O2}$ of 2% for both absorptive as well as emissive based responses. FIG. 11 shows that thermal emission can distort absorption measurements, and the effect of emission must be accounted for in certain cases. It also shows the OH vibration peaks in the vicinity of 1400 and 2500 nm. Such inherent optical absorption/emission peaks of the optical fiber may be used as the "thermal emission" source in some embodiments. Also in some embodiments, a combination of absorption and thermal emission based responses may be observed for illuminating light intensity of the same order of magnitude as the light intensity generated from the thermally emitting material. The effect of the thermal excitation of the OH vibration at 2247.19 nm is evident across the spectrum for absorption based measurements. FIG. 11 illustrates an example experiment performed allowing for emission compensation in the absorptive measurements and is shown in the case of Pd—$TiO_2$. The silica O—H vibration resonance heavily influences measurements in the vicinity of 2247.19 nm and should be considered in the interpretation of spectral data at high temperatures.

In conclusion, it has been determined that the materials 10 and the emissive film 50 can be substantially altered with environment chemistry, and, furthermore, that the altered emissivity can be observed with high isolation through tunneling by overlapping the thin-film near-field and optical fiber evanescent regions. This has been examined for films of high conductivity, hydrogen absorptivity, and LSPR activity at 1073 K. For the Pd—$TiO_2$ system a strong wavelength localized thermally excitable mechanism was observed in the UV-Vis, believed to be LSPR in origin. With the presented thermal spectroscopic technique, the thermal excitation of optical decay channels can be explored and examined, with profound simplicity, paving the way for exploring exciting research topics such as the thermal near-field, doping with rare earth elements, and by quantum size effects. The presented paradigm should be ubiquitous from basic science to use in energy generation and other high-temperature processes.

Example Embodiments: Free Space Configurations

In another exemplary embodiment, the particular thermal emitters 12 and/or the emissive film 60 could be applied to a surface or the like, such as a wall or the interior of a chemical reactor. In such cases, a camera could be applied to monitor chemical changes in the environment by detecting changes in the thermal emission from the surface resulting from modifications to the emissivity of the coating or sensing layer. Those of ordinary skill in the art will recognize various practical embodiments are contemplated based on the particular thermal emitters 12 and/or the emissive film 60 described herein. Note, this is distinct from standard IR optical pyrometry techniques in that the emissive film experiences a chemical composition dependent thermal emission. Here, the emissive film 60 produces the aforementioned thermal emissions, and the emissive film 60 is monitored by the camera or the like.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. An optical fiber sensor utilizing thermally emissive materials for chemical spectroscopy analysis, the sensor comprising:
    an emissive material, wherein the emissive material comprises the thermally emissive materials comprising one of $TiO_2$, Pd—$TiO_2$, and Au—$TiO_2$ nanocomposites, with varied properties comprising high conductivity, hydrogen absorptivity, and localized surface plasmon resonance (LSPR) based activity in nitrogen and in oxygen containing high-temperature environments, perovskite oxide, strontium titanate ($SrTiO_3$) or doped $SrTiO_3$, one of which emit electromagnetic radiation, wherein the electromagnetic radiation is modified due to chemical composition in an environment;
    the optical fiber sensor comprising a distributed optical fiber sensor with a plurality of emissive materials each operating at different wavelengths, the optical fiber operating without the emissive material probed with a light source external to the material; and
    a detector adapted to detect the electromagnetic radiation, wherein the electromagnetic radiation is indicative of the chemical interaction changes and hence chemical composition and/or chemical composition changes of the environment.

2. The sensor of claim 1, wherein the optical fiber sensor comprises an optical fiber sensor coupled to the detector, wherein the emissive material is one of deposited on a core or the end-face of the optical fiber, coated on the optical fiber, and integrated with the optical fiber to derive information about the chemical composition of the environment.

3. The sensor of claim 1, wherein the optical fiber sensor comprises an optical fiber coupled to the detector, wherein the emissive material is integrated with one of a core, a cladding, and a combination of the core and the cladding of the optical fiber to derive information about the chemical composition of the environment.

4. The sensor of claim 1, wherein the detector comprises two detectors each at opposite ends of an optical fiber of the optical fiber sensor which monitors an output from the emissive material to derive information about the chemical composition of the environment and spatial dependence of the chemical composition.

5. The sensor of claim 1, wherein the emissive material interacts with environment chemistry to provide an altered emissivity observed via high isolation with respect to background interferences through tunneling to the optical fiber sensor by overlapping the emissive material near-field and optical fiber evanescent regions.

6. The sensor of claim 1, wherein the emissive material is integrated with the optical fiber.

7. The sensor of claim 1, wherein the emissive material comprises one of the thermally emissive materials directly disposed to a material, the thermally emissive materials on an underlayer, the thermally emissive materials embedded in a matrix phase, a monolithic film with the thermally emissive materials, and the thermally emissive materials embedded in a multi-layer stack and/or overcoated by another thin film layer.

8. A method for chemical spectroscopy analysis with a sensor using thermally emissive materials, the method comprising:
emitting radiation by the thermally emissive materials responsive to thermal energy which is altered based on chemical interaction changes in an environment, the thermally emissive materials comprising one of $TiO_2$, $Pd$—$TiO_2$, and $Au$—$TiO_2$ nanocomposites, with varied properties comprising high conductivity, hydrogen absorptivity, and localized surface plasmon resonance (LSPR) based activity in nitrogen and in oxygen containing high-temperature environments, perovskite oxide, strontium titanate ($SrTiO_3$) or doped $SrTiO_3$; and
operating an optical fiber without the emissive material probed with a light source external to the material, the optical fiber sensor comprising a distributed optical fiber sensor with a plurality of emissive materials each operating at different wavelengths; and
detecting the radiation using a detector, wherein the electromagnetic radiation is indicative of the chemical interaction changes and hence chemical composition and/or chemical composition changes of the environment.

9. The method of claim 8, further comprising:
detecting the radiation by the detector coupled to an optical fiber of an optical fiber sensor, wherein the detector operates without the emissive material probed with a light source external to the material.

10. The method of claim 9, wherein the emissive material is one of deposited on a core of the optical fiber, coated on the optical fiber, and integrated with the optical fiber.

11. The method of claim 9, wherein the emissive material interacts with environment chemistry to provide an altered emissivity observed via high isolation through tunneling to the optical fiber by overlapping the emissive material near-field and optical fiber evanescent regions.

12. An optical fiber sensor using thermally emissive materials for chemical spectroscopy analysis, the sensor comprising:
an emissive material, wherein the emissive material comprises the thermally emissive materials comprising one of $TiO_2$, $Pd$—$TiO_2$, and $Au$—$TiO_2$ nanocomposites, with varied properties comprising high conductivity, hydrogen absorptivity, and localized surface plasmon resonance (LSPR) based activity in nitrogen and in oxygen containing high-temperature environments, perovskite oxide, strontium titanate ($SrTiO_3$) or doped $SrTiO_3$, one of which emit electromagnetic radiation, wherein the electromagnetic radiation is modified due to chemical composition in an environment;
the optical fiber sensor comprises a bundled fiber with a plurality of optical fibers therein with the emissive material to provide distributed sensing,
the optical fiber operating without the emissive material probed with a light source external to the material; and
a detector adapted to detect the electromagnetic radiation, wherein the electromagnetic radiation is indicative of the chemical interaction changes and hence chemical composition and/or chemical composition changes of the environment.

13. The sensor of claim 12, wherein the optical fiber sensor comprises an optical fiber coupled to the detector, wherein the emissive material is one of deposited on a core or the end-face of the optical fiber, coated on the optical fiber, and integrated with the optical fiber to derive information about the chemical composition of the environment.

14. The sensor of claim 12, wherein the optical fiber sensor comprises an optical fiber coupled to the detector, wherein the emissive material is integrated with one of a core, a cladding, and a combination of the core and the cladding of the optical fiber to derive information about the chemical composition of the environment.

15. The sensor of claim 12, wherein the detector comprises two detectors each at opposite ends of an optical fiber of the optical fiber sensor which monitors an output from the emissive material to derive information about the chemical composition of the environment and spatial dependence of the chemical composition.

16. The sensor of claim 12, wherein the optical fiber sensor comprises a distributed optical fiber sensor with a plurality of emissive materials each operating at different wavelengths.

* * * * *